United States Patent [19]
Hiller et al.

[11] Patent Number: 5,048,322
[45] Date of Patent: Sep. 17, 1991

[54] HEATED COLUMN INLET GAS CHROMATOGRAPHY METHOD AND APPARATUS

[75] Inventors: Joseph F. Hiller; Terrence McCabe; Paul L. Morabito, all of Midland, Mich.

[73] Assignee: The Dow Chemical Company, Midland, Mich.

[21] Appl. No.: 402,327

[22] Filed: Sep. 5, 1989

[51] Int. Cl.⁵ .............................................. G01N 30/30
[52] U.S. Cl. .................................. 73/23.41; 73/23.39
[58] Field of Search .................. 73/23.1, 23.25, 23.39, 73/23.41, 23.42; 422/89

[56] References Cited
U.S. PATENT DOCUMENTS

| | | | |
|---|---|---|---|
| 3,181,344 | 5/1965 | Burow | 73/23.1 |
| 3,225,520 | 12/1965 | Burow | 73/23.1 X |
| 3,225,521 | 12/1965 | Burow | 73/23.1 X |
| 4,004,881 | 1/1977 | Ligon, Jr. | 73/23.1 |
| 4,057,998 | 11/1977 | Moreaux | 73/23.1 |
| 4,367,645 | 1/1983 | Froment | 73/23.1 |
| 4,442,217 | 4/1984 | Deans | 73/23.1 X |
| 4,805,441 | 2/1989 | Sides et al. | 73/23.1 |

OTHER PUBLICATIONS

G. Schomberg et al., HRC & CC; 5 (1982); 565-567.
W. Vogt et al., J. of Chromatogr., 174 (1979); 437-439.
P. Morabito et al., J. of HRC, 12 (1989); 347-349.
P. Kirschmer et al., HRC & CC; 7 (1984), 306-311.
S. Blomberg et al., J. of HRC, 12 (1989); 294-299.
K. Grob, "On-Column Injection in Capillary Gas Chromatography"; Huethig, N.Y. (1987); 357-583.
F. Poy et al., HRC & CC; 5 (1982), 355-359.
Th. Noy et al., HRC & CC; 11 (1988), 181-186.
H. Cortes et al., J. Microcolumn Separations, 1 (1989); 28-34.

Primary Examiner—Hezron E. Williams
Assistant Examiner—Joseph W. Roskos
Attorney, Agent, or Firm—Burke M. Halldorson; Timothy S. Stevens

[57] ABSTRACT

The invention describes a large volume on-column gas chromatographic method for analyzing trace levels of high molecular weight and polar compounds in a sample and an apparatus for performing the method. A column inlet coupled to an analytical column is heated rapidly to concentrate difficult to chromatograph compounds onto the analytical column resulting in an increase in the detectability of the compounds.

20 Claims, 2 Drawing Sheets

HEATED COLUMN INLET GAS CHROMATOGRAPHY METHOD AND APPARATUS

BACKGROUND OF INVENTION

The invention is in the field of capillary gas chromatography and more particularly in the field of on-column injection gas chromatography using a column inlet.

The ultimate goal of gas chromatography would be to achieve baseline separation of any number of components in a mixture, to identify each component at any concentration, and to carry out the separation instantaneously. While this goal may never be realized, great strides are continually being made in improving separations, in increasing sensitivity, and reducing analysis time.

The introduction of capillary columns represented a major achievement in gas chromatography resulting in marked improvements in separability, sensitivity, and reduced analysis times. Capillary gas chromatography was further advanced by the innovation of the retention gap, a column inlet connected to an analytical column, having relatively low retentive power with respect to the active phase of the analytical column, usually being deactivated but uncoated with stationary phase. (See Grob's "On-Column Injection in Capillary Gas Chromatography", Huethig, N.Y. [1987], pg 583, herein incorporated by reference.) The retention gap has become a preferred means for injecting considerably larger volumes of sample into a capillary gas chromatographic column than previously thought possible, resulting in as much as a several hundred-fold improvement in the signal to noise ratio for the analysis of solutes in the sample at a given concentration. There is no suggestion in the literature that a column inlet with equal or higher retentive power with respect to the active phase of the analytical column could be used for large volume on-column injection and, in fact, Grob (supra, pg 363) teaches away from this practice.

The practice of large volume on-column injection involves introducing a large volume of sample comprising a solvent and a component of interest into a retention gap usually at a temperature close to the boiling point of the solvent at atmospheric pressure. It is believed that a thin layer of the sample forms on the walls of the retention gap as a result of the rapid passage of carrier gas through the system. The solvent elutes first onto the analytical column followed by the volatile analytes which form a concentrated band on the analytical column. This concentration of volatile analytes leads to correspondingly sharp peaks in the chromatogram.

While retention gap technology has enabled large sample volumes of many types of compounds to be successfully chromatographed, certain classes of compounds, namely compounds not mobile in the retention gap at temperatures near the boiling point of the solvent (hereinafter referred to as non-volatile compounds), are still difficult to chromatograph. Unlike the volatile analytes, these non-volatile compounds do not concentrate at the analytical column at temperatures close to the boiling point of the solvent but instead, tend to remain spread along the wall of the retention gap. Even upon ramping the temperature of the oven, the peaks corresponding to these compounds are often broad and difficult to integrate. The ability to concentrate these compounds at the front of the analytical column would clearly be advantageous and would result in an improvement in sensitivity as well as repeatability of integrated signal.

SUMMARY OF THE INVENTION

The present invention solves the problems inherent in the prior art of large volume on-column capillary gas chromatography when chromatographing a sample which includes a non-volatile compound. Furthermore, the invention dispels the notion that large sample volumes are unsuitable for capillary columns other than retention gaps. The invention is a large volume injection gas chromatographic method of analyzing for a component within a sample which comprises a solvent and the component of interest, the method comprising the steps of:

(a) flowing a stream of carrier gas through a column inlet communicating with an analytical column;

(b) introducing at least 10 $\mu l$ of sample into the column inlet; and (c) separately controlling the temperature of said column inlet from the temperature of said analytical column.

The retention power of the column inlet is immaterial and the inlet can be a retention gap or a capillary column of higher retentive power than the analytical column.

Another aspect of the invention relates to an improved gas chromatograph suitable for large volume on-column injection comprising a retention gap, an analytical column, and a detector communicating in series and a means for controlling the temperature of the analytical column, the improvement comprising a second means for controlling the temperature of said retention gap whereby said retention gap can be controlled at a temperature different than the temperature of the analytical column.

DETAILED DESCRIPTION OF THE INVENTION

Figure 1:
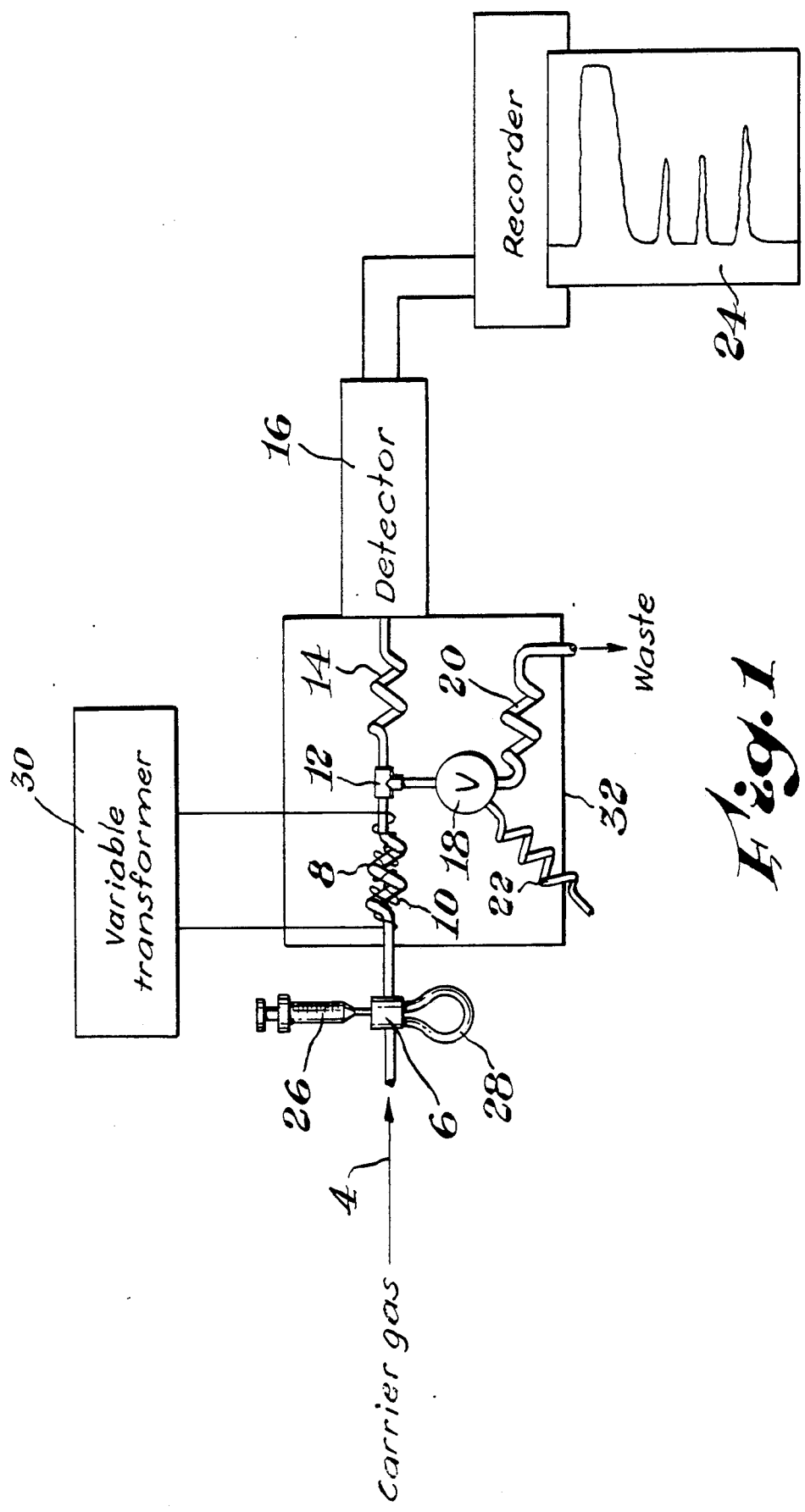
FIG. 1 is a schematic of an apparatus that can be used to practice the method of the present invention.

Referring to FIG. 1, therein is shown a schematic drawing of the preferred embodiment of a gas chromatography system suitable for performing the present method. The system includes a supply of carrier gas 4 such as helium. The carrier gas 4 is flowed through a loop-type injection valve 6, a column inlet 8, a three-way union 12, an analytical column 14, and into a detector 16. The three-way union 12, while preferred, is not an essential element of the invention, and a simple connecting union could be used. A resistive wire 10 surrounds the exterior surface of the column inlet 8. The three-way union 12 is connected also to a two-way divert valve 18. The two-way divert valve 18 is also connected to a vent restrictor 20 and a bleed restrictor 22. The column inlet 8, three-way union 12, analytical column 14, two-way divert valve 18, vent restrictor 20 and bleed restrictor 22 are all contained in an oven 32. A recorder 24 is connected to the detector 16 for recording chromatograms. A variable transformer 30 supplies power to the resistive wire 10.

The present invention is suitable for the injection of relatively large volumes of liquid sample preferably at least 10 µl, more preferably from 20 µl, and most preferably from 50 µl, and preferably up to 1000 µl, more preferably up to 500 µl and most preferably up to 300 µl, comprising a volatile solvent such as hexane and a component of interest such a pentachlorophenol. While the invention is suitable for all gas chromatographable compounds, the detectability of polar compounds such as alcohols and phenols and high molecular weight non-polar compounds with boiling points not less than 100° C. higher than the boiling point of the solvent at atmospheric pressure, such as di-n-octyl phthalate, is particularly enhanced.

It is true that the detectability of these non-volatile compounds could be enhanced by merely concentrating the sample by pre-evaporation. However, pre-evaporation requires hours of tedious labor, which in turn increases the possibility of exposure of sample to the analyst, and usually results in the loss of volatile analytes which the sample may comprise. On the other hand, sample preparation is greatly facilitated using the method of the invention, and the increased sensitivity of the response attained for the non-volatile compounds do not adversely affect the response of the volatile compounds. Thus, the greatest utility of the separately heated column inlet is appreciated when the sample comprises a mixture of volatile and non-volatile analytes.

The choice of the solvent is not critical but volatile solvents of low to medium polarity such as hexane, acetone, diethyl ether, and methylene chloride are most commonly used. However, even polar solvents such as ethanol and water can be used.

A resistive wire is the preferred means for separately heating the column inlet, but other means such as enclosing the column inlet in an internal oven or heating by microwave would be effective as well. It is also perfectly acceptable to situate the column inlet outside the oven of the gas chromatograph.

The column inlet can also serve as an interface between the analytical column and a liquid chromatograph system. The teaching of an LC-GC interface which allow the introduction of large sample volumes onto a capillary column is described by Noy et al., HRC & CC, 11 (1988), 181-186 and Cortes et al., J. Microcolumn Separations, 1 (1989), 28-34, and is incorporated by reference into the disclosure.

Referring again to FIG. 1, syringe 26 is used to fill the sample loop 28 with sample. The volume of the sample loop 28 is preferably at least 10 µl because carry over problems can be significant at volumes less than 10 µl. When the valve 6 is actuated the sample in the loop 28 is injected into the column inlet 8 by the carrier gas 4.

The solvent elutes onto the analytical column 14 first followed by volatile analytes which form a concentrated band on the analytical column. In the preferred mode of the method of the invention, the carrier flow 4 is diverted primarily to vent by switching valve 18 to allow carrier gas 4 to pass through vent restrictor 20 at a rate which is about 10-50 times and most preferably about 30 times greater than the rate at which carrier gas 4 passes through the analytical column 14 so that a large portion of the solvent is diverted to waste outside the oven 32 before being eluted on the analytical column. The reason for diverting flow is to avoid overloading the detector with solvent. An additional benefit of sample diversion is that volatile analytes are better resolved in the resultant chromatogram therefrom. As mentioned previously, if no volatile analytes are present in the sample, diverting of solvent is not essential. The actual amount of solvent diverted to waste is determined by trial and error and corresponds to approximately the largest amount of solvent that can be diverted to waste which does not result in the diversion to waste of measurable amounts of analytes.

After the desired amount of solvent is diverted to waste, valve 18 is switched to allow carrier 4 to pass through the bleed restrictor 22 at a rate which is about one-tenth to about one one-hundredth and preferably one-fiftieth the rate at which the carrier 4 flows through the analytical column 14. The reason that a small portion of the carrier gas continues to be diverted to vent through the bleed restrictor 22 at this point is to prevent the backup of solvent into the analytical column 14.

Concurrent with the switching of valve 18, the resistive wire 10 surrounding the column inlet 8 is heated rapidly by the variable transformer 26. First, the temperature of the column inlet is raised most preferably from about the temperature of the boiling point of the solvent at atmospheric pressure up to about 270° C. and preferably between about 150° C.–270° C. The initial temperature of the column inlet is non-critical and final temperatures above 270° C. may be employed provided no detrimental effects such as decomposition of the sample or of the column inlet occur. The selection of the temperature profile of the column inlet (to what temperature and over what period of time it is heated) is generally based on the boiling points of the solvent and the analytes.

Second, the analytical column 14 is heated by the oven 32 from about the temperature of the boiling point of the solvent at atmospheric pressure to a designated temperature (typically about 200° C.–350° C.) for a period of time necessary to elute the component of interest through the analytical column 14 with the desired result. As for the case of the column inlet 8, the selection of the temperature profile of the oven is generally based on the boiling points of the solvent and the analytes.

Separately controllable heating sources for the column inlet and the analytical column are necessary to achieve the desired result because the non-volatile analytes will otherwise spread out in the analytical column, not concentrate thereon. The concentrative effect is achieved by transferring the non-volatile analytes from a relatively hot zone (the column inlet) to a relatively cold one (the analytical column).

The separate heating of the column inlet to concentrate the component or components of interest onto the analytical column resulting in peaks that are more detectable and more reproducible in replicate analyses is the essence of the invention. As will be shown in the first example, the separate heating of a retention gap form of column inlet leads to a significant improvement in signal to noise ratio of the components of interest. An added benefit of separately heating the retention gap is that its lifetime is often increased dramatically. It will be clear from the second example that the column inlet need not have less retentive power than the analytical column.

EXAMPLE 1

A system generally similar to that shown in FIG. 1 is assembled. The head pressure of the carrier gas 4 is 13 PSI helium. A Valco six port (#ATC6WP) pneumatically actuated valve 6 is attached to a Hewlett Packard 5890 gas chromatograph 2 having a flame ionization detector 16. The valve 6 is fitted with a 100 $\mu$l loop 28. The column inlet 8 is a 10 meter×0.53 mm ID tube (Restek #10032). The analytical column 14 is a 30 meter ×0.32 mm ID Restek Rtx-5, 1 $\mu$m film coating, fused silica capillary column (Restek #10254). The retention gap 8 is wrapped with glass tape from Fisher (#01-472-A), 7.7 ft of Chromel A 24 gauge wire (Hosking MFG CO. #155402D), 1.682 ohms/ft and then insulated again with glass tape from Fisher (#01-472-A). A variable transformer 30 is used to supply power to the resistive wire 10 wrapped around the retention gap 8. The retention gap 8 is connected to the analytical column 14 using a Hewlett Packard Press Fit Y 12 (#50412172); The divert valve 18 is a Valco 4-port (#A6N-4WT) pneumatically actuated valve. The vent restrictor 20 is a fused silica capillary tube of 0.53 mm ID ×0.5 meter and the bleed restrictor 22 is a fused silica capillary tube of 9 cm ×0.025 mm ID.

The temperature of the injector through which the retention gap 8 is routed is set to 100° C. and the detector 16 is set to 250° C. The temperature of the oven 32 is initially 65° C. The sample contains an unknown amount of m-dichlorobenzene, 1,3,5-trichlorobenzene, 2,6-dichlorophenol, 2,4,6-trichlorophenol and about 440 parts per billion of pentachlorophenol. At the time of sample injection, the helium 4 flows concurrently through the vent restrictor 20 into waste and the analytical column 14. The flow of helium 4 is 16.5 ml/min through the vent restrictor 20 and 0.6 ml/min through the analytical column 14.

About 1.3 minutes after the start of the of the chromatographic run, the divert valve 18 is switched so that the helium 4 is flowing concurrently through the bleed resistor 22 and the analytical column 14. The flow of helium 4 is 0.04 ml/min through the bleed restrictor 22 and 1.6 ml/min through the analytical column. Concurrent with the switching of the divert valve 18, the resistive wire 10 surrounding the retention gap 8 is heated by the variable transformer 30. The temperature of the retention gap 8 is raised from 65° C. to 170° C. in 2 minutes and is maintained at 175° C. for an additional 6 minutes. The temperature of the over 32 is programmed to stay at 65° C. for the first 7 minutes of the chromatographic run then to ramp at a rate of 10° C./min until a final temperature of 250° C. is reached. The rampiong of the oven temperature increases the temperature of the resistive wire 10 and when the wire reaches 250° C. the variable transformer 30 is turned off.

Figure 2A:
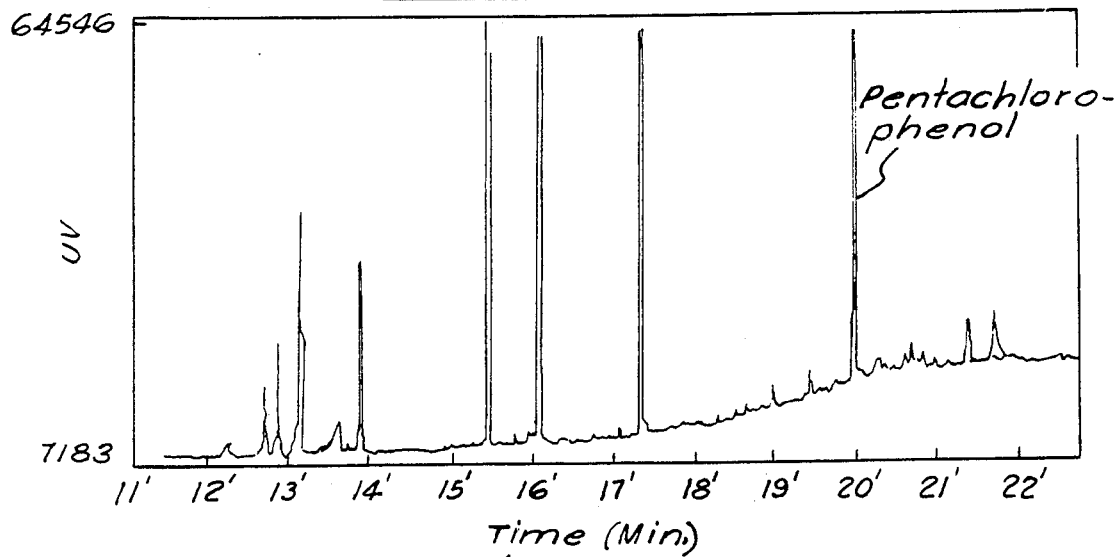
FIG. 2a is a chromatogram of a mixture comprising about 440 ppb pentachlorophenol in hexane which is injected into a retention gap which has been heated separately from the analytical column.
Figure 2B:
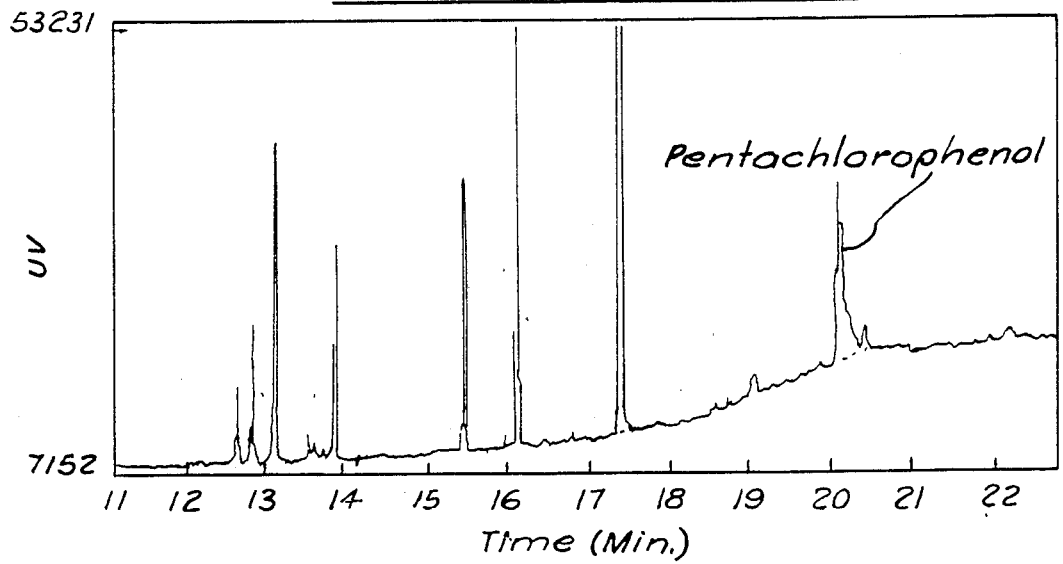
FIG. 2b is a chromatogram of the same mixture described in FIG. 2a wherein the mixture is injected into a retention gap which is not heated separately from the analytical column.

The resultant chromatogram is shown in FIG. 2a and a chromatogram of the same mixture injected into an unheated retention gap is shown in FIG. 2b. The improvement in signal to noise is approximately a factor of three as shown in Table 1 below.

TABLE 1

| Comparison of Peak Heights and Areas | | | |
|---|---|---|---|
| | Peak Heights | Peak Areas | S/N Ratio |
| Unheated | 19,055 | 98.658 | 123 |

TABLE 1-continued

| Comparison of Peak Heights and Areas | | | |
|---|---|---|---|
| | Peak Heights | Peak Areas | S/N Ratio |
| Heated | 57,182 | 110,553 | 306 |

EXAMPLE 2

As in Example 1, a system generally similar to that shown in FIG. 1 is assembled. The head pressure of the carrier gas 4 is 12 PSI helium. A Valco six port (#ATC6WP) pneumatically actuated valve 6 is attached to a Varian 3700 gas chromatograph 2 having a flame ionization detector 16. The valve 6 is fitted with a 50 $\mu$l loop 28. The column inlet 8 is a 15 meter×0.53 mm ID tube coated with 1.5 $\mu$m film of DB-5 (J & W Scientific, 125-5012). The analytical column 14 is a 30 meter ×0.32 mm ID Restek Rtx-5, 0.25 $\mu$m film coating, fused silica capillary column (Restek #10224). This combination is an example of using a column inlet having higher retentive power than the analytical column.

The column inlet 8 is wrapped with 9.6 ft of double glass insulated Nichrome 60 29 gauge wire (Pelican Wire Co.), 5.7 ohms/ft and then insulated with glass tape from Fisher (#01-472-A). A variable transformer 30 is used to supply power to the resistive wire 10 wrapped around the column inlet 8. The column inlet 8 is connected to the analytical column 14 using a Hewlett Packard Press Fit Y 12 (#5041-2172). The divert valve 18 is a Valco 4-port (#A6-N4WT) pneumatically actuated valve. The vent restrictor 20 is a fused silica capillary tube of 0.32 mm ID ×0.93 meter and the bleed restrictor 22 is a fused silica capillary tube of 40 cm ×0.05 mm ID.

The temperature of the injector through which the column inlet 8 is routed is set to 100° C. and the detector 16 is set to 250° C. The temperature of the oven 32 is initially 60° C. The sample contains 1000 ppb concentration of m-dichlorobenzene, 1,3,5-trichlorobenzene, 2,6-diehlorophenol, 2,4,6-trichlorophenol and pentachlorophenol. At the time of sample injection, the helium 4 flows concurrently through the vent restrictor 20 into waste and the analytical column 14. The flow of helium 4 is 15.6 ml/min through the vent restrictor 20 and 1.04 ml/min through the analytical column 14.

About one minute after the start of the of the chromatographic run, the divert valve 18 is switched so that the helium 4 is flowing concurrently through the bleed restrictor 22 and the analytical column 14. The flow of helium 4 is 0.07 ml/min through the bleed restrictor 22 and 2.3 ml/min through the analytical column. At 1.5 minutes after the injection, the resistive wire 10 surrounding the column inlet 8 is heated by the variable transformer 30. The temperature of the column 8 is raised from 65° C. to 250° C. in ~2 minutes and is maintained at 250° C. for an additional 6.5 minutes. The temperature of the oven 32 is programmed to stay at 65° C. for the first 7 minutes of the chromatographic run then to ramp at a rate of 8° C./min until a final temperature of 250° C. is reached.

The improvement in signal to noise for the peak corresponding to 1,3,5-trichlorobenzene is approximately a factor of six as shown in Table 2 below.

TABLE 2

Comparison of Peak Heights and Areas for Peak 3 (1,3,5-trichlorobenzene)

| | Peak Heights | Peak Areas | S/N Ratio |
|---|---|---|---|
| Unheated | 4,844 | 232,645 | 440 |
| Heated | 69,283 | 289,284 | 2,470 |

What is claimed is:

1. A gas chromatograph suitable for large volume on-column injection comprising a retention gap, an analytical column, and a detector communicating in series and a first means for controlling the temperature of said analytical column, the improvement comprising:
    a second means for controlling the temperature of said retention gap whereby said retention gap can be controlled at a temperature different than the temperature of the analytical column.

2. The chromatograph of claim 1 wherein the means for controlling the temperature of said analytical column is an oven.

3. The chromatograph of claim 2 wherein said means for selectively controlling the temperature of said retention gap comprises a resistive wire.

4. The chromatograph of claim 3 wherein said resistive wire surrounds the exterior surface of said retention gap.

5. The chromatograph of claim 4 wherein said resistive wire surrounds at least 50% of the exterior surface of said retention gap.

6. The chromatograph of claim 4 wherein the means for communicating said analytical column and said retention gap comprises a three-way union.

7. The chromatograph of claim 6 wherein said three-way union communicates simultaneously with said analytical column, said retention gap, and a means to vent sample.

8. The chromatograph of claim 7 wherein said means to vent sample is a two-way automated valve.

9. The chromatograph of claim 8 wherein said two-way automated valve additionally communicates alternately upon switching with a first sample flow restrictor and a second sample flow restrictor wherein the restriction of said first sample flow restrictor is different than the restriction of said second sample flow restrictor.

10. The chromatograph of claim 9 wherein said retention gap, said three-way union, said automated valve, said resistive wire, and said first and second restrictors are contained in said oven.

11. The chromatograph of claim 1 wherein said retention gap comprises a capillary tube uncoated with stationary phase.

12. A large volume injection gas chromatographic method of analyzing for a component within a sample which comprises a solvent and the component of interest, the method comprising the steps of:
    (a) flowing a stream of carrier gas through a column inlet communicating with an analytical column, the column inlet selected from the group consisting of a retention gap and an unpacked capillary column;
    (b) introducing at least 10 $\mu$l of sample into the column inlet; and
    (c) separately controlling the temperature of said column inlet from the temperature of said analytical column.

13. The method of claim 12 wherein a substantial portion of the solvent is diverted predominantly to waste, thereafter, increasing the temperature of said column inlet, and then increasing the temperature of said analytic column.

14. The method of claim 13 wherein said column inlet is a retention gap.

15. The method of claim 14 wherein the component of interest has a boiling point at atmospheric pressure of at least 75° C. higher than the boiling point of the solvent at atmospheric pressure.

16. The method of claim 15 wherein at least about 50 $\mu$l of sample is introduced into said column inlet.

17. The method of claim 13 wherein said column inlet is a coated capillary column of at least equal retentive power with respect to said analytical column.

18. The method of claim 17 wherein the component of interest has a boiling point at atmospheric pressure of at least 100° C. higher than the boiling point of the solvent at atmospheric pressure.

19. The method of claim 13 wherein the component of interest has a boiling point at atmospheric pressure of at least about 50° C. higher than the boiling point of the solvent at atmospheric pressure.

20. The method of claim 13 wherein at least about 20 $\mu$l of sample is introduced into said column inlet.

* * * * *